United States Patent
Reykhert

(10) Patent No.: US 12,249,418 B2
(45) Date of Patent: Mar. 11, 2025

(54) SMART PATCH FOR MONITORING HEALTH METRICS

(71) Applicant: ANEXA LABS LLC, Mountain View, CA (US)

(72) Inventor: Alexey Reykhert, Omsk (RU)

(73) Assignee: ANEXA LABS LLC, Mountain View, CA (US)

( * ) Notice: Subject to any disclaimer, the term of this patent is extended or adjusted under 35 U.S.C. 154(b) by 0 days.

(21) Appl. No.: 17/235,650

(22) Filed: Apr. 20, 2021

(65) Prior Publication Data

US 2021/0241900 A1   Aug. 5, 2021

Related U.S. Application Data

(63) Continuation of application No. 17/103,666, filed on Nov. 24, 2020, now Pat. No. 11,024,423, which is a
(Continued)

(51) Int. Cl.
*G16H 40/63* (2018.01)
*A61B 5/00* (2006.01)
(Continued)

(52) U.S. Cl.
CPC ............ *G16H 40/63* (2018.01); *A61B 5/282* (2021.01); *A61B 5/6831* (2013.01); *A61B 5/6832* (2013.01); *G16H 50/30* (2018.01)

(58) Field of Classification Search
CPC . A61B 5/6833; A61B 5/04085; A61B 5/6831; A61B 5/6832; A61B 2562/164
(Continued)

(56) References Cited

U.S. PATENT DOCUMENTS 7,020,508 B2   3/2006   Stivoric
10,299,691 B2   5/2019   Hughes
(Continued)

FOREIGN PATENT DOCUMENTS

WO   2010/107913 A2   9/2010
WO   2010/111788 A1   10/2010
WO   2019/050778 A1   3/2019

OTHER PUBLICATIONS

International Search Report and Written Opinion in International Patent Application No. PCT/US2020/056884, mailed Nov. 30, 2020 (11 pages).

*Primary Examiner* — Joseph M Dietrich
*Assistant Examiner* — Michael T. Holtzclaw
(74) *Attorney, Agent, or Firm* — NIXON PEABODY LLP

(57) ABSTRACT

A smart patch includes a computing device to monitor user health metrics. The smart patch also includes an adhesive coupled to a cradle with an opening and coupled to at least two electrodes capable of electrically coupling to the user. The computing device contains one or more sensors, a battery and a sensor window. The sensors are configured to interface with the user to generate physiological data associated with the user's health. The battery is configured to power the sensors. The computing device is removably coupled to the cradle. The cradle is configured to engage the computing device securing the computing device to the adhesive. The electrodes electrically couple to the user's skin and conduct electrical signals between the user and the computing device.

16 Claims, 10 Drawing Sheets

Related U.S. Application Data continuation of application No. 16/663,915, filed on Oct. 25, 2019, now Pat. No. 10,878,959.

(51) Int. Cl.
*A61B 5/282* (2021.01)
*G16H 50/30* (2018.01)

(58) Field of Classification Search
USPC .................................. 600/372, 390–391, 301
See application file for complete search history.

(56) References Cited

U.S. PATENT DOCUMENTS

| | | | | |
|---|---|---|---|---|
| 10,419,050 | B1* | 9/2019 | Cetinoneri | H04B 1/0475 |
| 10,878,959 | B1* | 12/2020 | Reykhert | A61B 5/6832 |
| 11,024,423 | B2* | 6/2021 | Reykhert | A61B 5/282 |
| 2005/0090725 | A1* | 4/2005 | Page | A61B 8/4281 |
| | | | | 600/344 |
| 2008/0210809 | A1* | 9/2008 | Arlton | B64C 39/024 |
| | | | | 244/17.11 |
| 2012/0088999 | A1 | 4/2012 | Bishay | |
| 2013/0116534 | A1 | 5/2013 | Woo | |
| 2014/0051946 | A1 | 2/2014 | Arne | |
| 2014/0100432 | A1* | 4/2014 | Golda | A61B 5/02141 |
| | | | | 600/595 |
| 2014/0206977 | A1 | 7/2014 | Bahney | |
| 2015/0094558 | A1 | 4/2015 | Russell | |
| 2015/0195433 | A1* | 7/2015 | Lin | H04N 23/54 |
| | | | | 348/374 |
| 2015/0238094 | A1 | 8/2015 | Lai | |
| 2016/0106950 | A1* | 4/2016 | Vasapollo | A61M 21/02 |
| | | | | 600/27 |
| 2016/0192856 | A1 | 7/2016 | Lee | |
| 2016/0302674 | A1 | 10/2016 | Moyer et al. | |
| 2016/0317057 | A1* | 11/2016 | Li | A61B 5/6833 |
| 2017/0172413 | A1 | 6/2017 | Chakravarthy | |
| 2017/0188872 | A1 | 7/2017 | Hughes | |
| 2019/0059757 | A1* | 2/2019 | Balda | A61B 5/291 |
| 2020/0282225 | A1* | 9/2020 | Kumar | A61N 1/0492 |
| 2021/0105026 | A1* | 4/2021 | Schwerg | H04B 1/0458 |

* cited by examiner

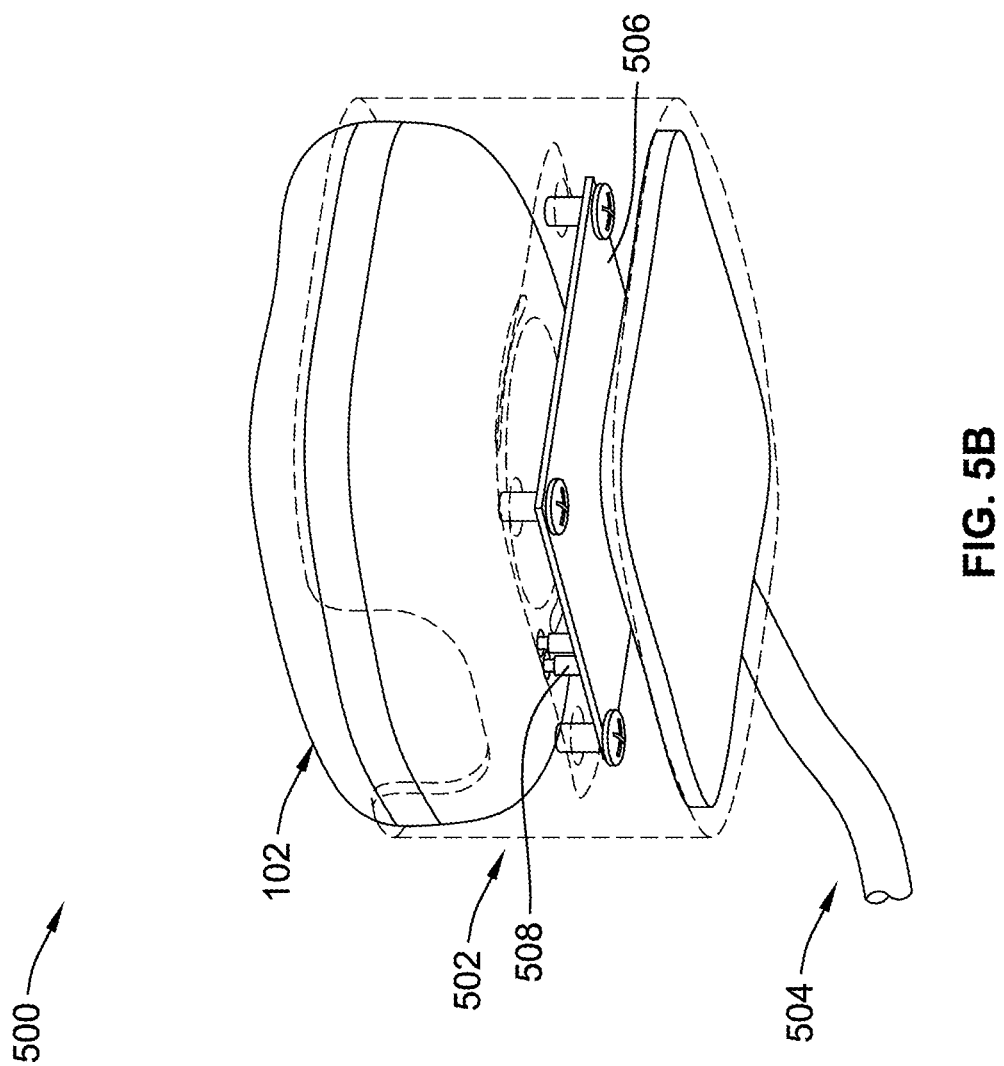

SMART PATCH FOR MONITORING HEALTH METRICS

CROSS-REFERENCE TO RELATED APPLICATIONS

This application is a continuation of U.S. patent application Ser. No. 17/103,666, filed Nov. 24, 2020, which is a continuation of U.S. patent application Ser. No. 16/663,915, filed Oct. 25, 2019, each of which is hereby incorporated by reference herein in its entirety.

TECHNICAL FIELD

The present disclosure relates to monitoring health metrics of a user and more specifically to systems, methods, and devices that integrate a plurality of sensors in a compact form factor to capture measurements for determining health of the user.

BACKGROUND

Wearable devices are becoming ubiquitous in society. These devices are worn on the human body and are designed to measure one or more parameters. Smartwatches and smart patches are examples of wearable devices that can have multiple sensors and that can pair to a smartphone. Smartwatches can provide estimates of activity level of a human in the form of number of steps the human takes per day. Smartwatches can provide a heart rate of the human, a location of the human, and so on. Smart patches and smartwatches can have similar functionality, but a smart patch can be provided without a display. Unlike smartwatches which can be removed anytime by unbuckling a strap or stretching an elastic band, smart patches typically attach to the user via some adhesive. Removing a smart patch can be uncomfortable for the user and can lead to damaging the device.

SUMMARY

Some implementations of the present disclosure provide an electronic device for measuring health metrics of a user. The electronic device includes: a housing including a housing window; one or more sensors provided within the housing, the one or more sensors configured to interface with the user to generate physiological data associated with the health metrics of the user; a battery provided within the housing, the battery configured to power the one or more sensors; and a base removably coupled to the housing, the base including an inner surface, an outer surface, and a base window. The inner surface of the base is configured to engage the housing and secure the housing to the base, wherein when the housing is secured to the base, the base window overlaps the housing window such that the one or more sensors interface with the user via the base window and the housing window. The electronic device further includes a set of electrodes removably coupled to the base such that when the housing is secured to the base, the set of electrodes is configured to conduct electrical signals of the housing across the base, facilitating movement of the electrical signals through the base, between the inner surface of the base and the outer surface of the base.

The foregoing and additional aspects and implementations of the present disclosure will be apparent to those of ordinary skill in the art in view of the detailed description of various embodiments and/or implementations, which is made with reference to the drawings, a brief description of which is provided next.

BRIEF DESCRIPTION OF THE DRAWINGS

The foregoing and other advantages of the present disclosure will become apparent upon reading the following detailed description and upon reference to the drawings.

FIG. 5B illustrates an interior of the charging station when coupled to the body of the electronic device of FIG. 1A, according to some implementations of the present disclosure.

Figure 1A:
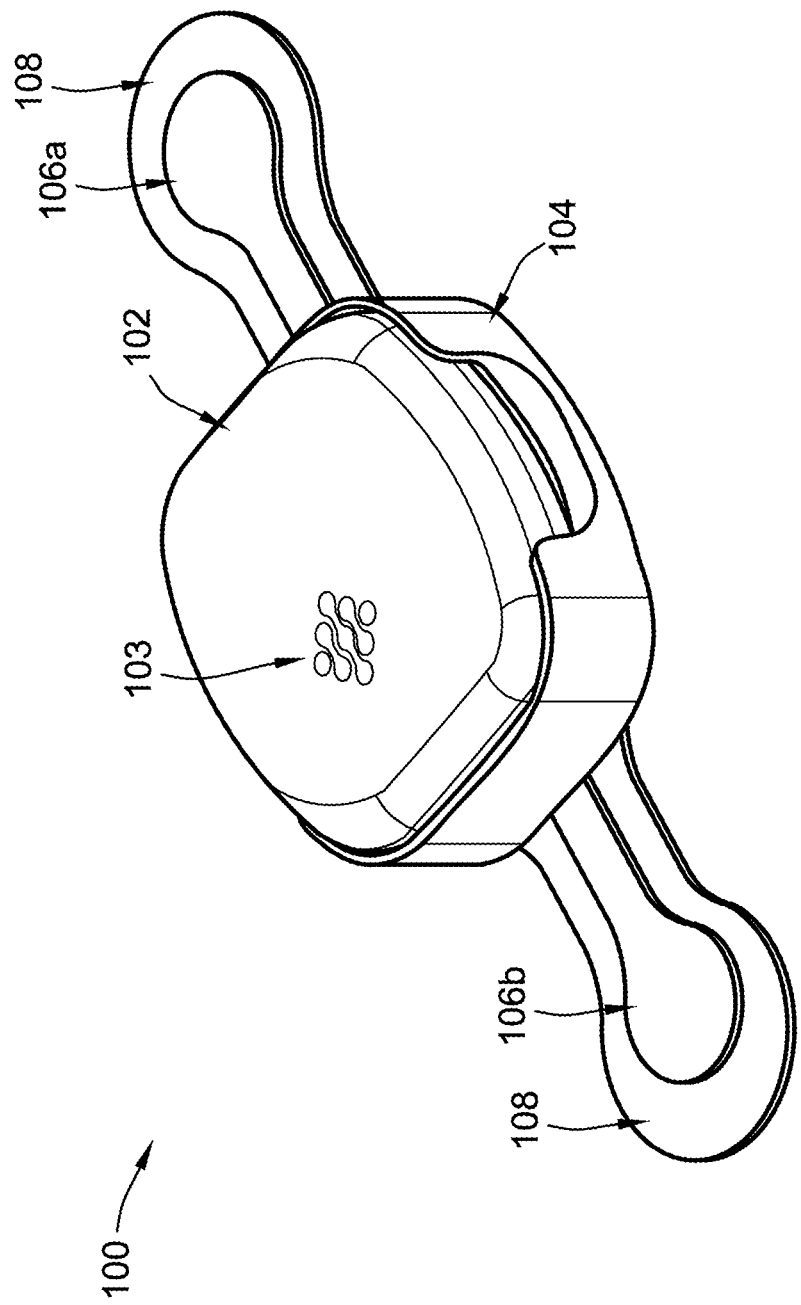
FIG. 1A illustrates an electronic device for monitoring health metrics of a user, according to some implementations of the present disclosure.

While the present disclosure is susceptible to various modifications and alternative forms, specific implementations have been shown by way of example in the drawings and will be described in detail herein. It should be understood, however, that the present disclosure is not intended to be limited to the particular forms disclosed. Rather, the present disclosure is to cover all modifications, equivalents, and alternatives falling within the spirit and scope of the present disclosure as defined by the appended claims.

DETAILED DESCRIPTION

Embodiments of the present disclosure provide an electronic device to measure one or more health metrics of a user. The electronic device can obtain the measurements in an unintrusive manner. The electronic device can perform both contact and non-contact measurements. The non-contact measurements can be achieved via electromagnetic signaling. The contact measurements can be achieved via electrodes removably coupled to the electronic device. In some embodiments, the electronic device has a small form factor with a long battery life. In some embodiments, the electronic device can be modified to perform invasive measurements.

Embodiments of the present disclosure provide an electronic device that can attach to a user with an adhesive holding electrodes of the electronic device in place. The adhesive electrodes are separable from an electronics compartment of the electronic device such that a battery in the electronics compartment can be charged while the adhesive electrodes are still attached to the user. A configuration as such can provide several advantages over conventional devices. For example, the electronics compartment can be removed to charge the battery without having to disturb the adhesive holding the electrodes in place on the skin of the user. This way, frequent and multiple charges can be performed without having to remove and re-attach the adhesive electrodes.

Adhesive electrode waste is reduced compared to conventional devices. For example, a smart patch with adhesive electrodes should be re-attached to the user with an adhesive if removed for charging. Conventional smart patches typically involve removing the adhesive electrode when removing a smart patch device and then re-attaching the smart patch device. The process of removing an adhesive electrode can damage the adhesive electrode. Depending on the number of charging events, new adhesive electrodes may be required for each re-attachment. Costs associated with new adhesive electrodes can thus add up.

Furthermore, detaching and reattaching adhesive electrodes on the skin of the user can adversely affect quality of skin around where the smart patch is placed. More skin cells than usual may be lost. Plus, the skin can become sensitive after each removal of an adhesive electrode, making the removal and re-attachment of the smart patch an uncomfortable event for the user. As such, embodiments of the present disclosure provide a system and method for charging an electronic device without having to detach adhesive electrodes of the electronic device from the user. An advantage to having the adhesive electrodes in one position is that once the electronic device is reattached to the electrodes, the electronic device is configured to make measurements at the exact same location. As such, the effect of noise relating to minor location changes is reduced.

Referring to FIG. 1A, an electronic device 100 for monitoring health metrics of a user is illustrated according to some implementations of the present disclosure. The electronic device 100 includes a body 102, a base 104, one or more electrodes 106a, 106b . . . , and an adhesive 108 for holding the electrodes 106 in place. The body 102 includes electronic components encased in a housing. The body 102 is removably coupled to the base 104. The base 104 can receive the body 102, allowing the body 102 to pressure fit snugly in the base 104. The body 102 can include a logo 103. The logo 103 can include one or more LED lights. The logo 103 can include a frosted and/or opaque material like plastic, crystal glass, etc., which is backlit with LED lights to give a translucent appearance.

Figure 1B:
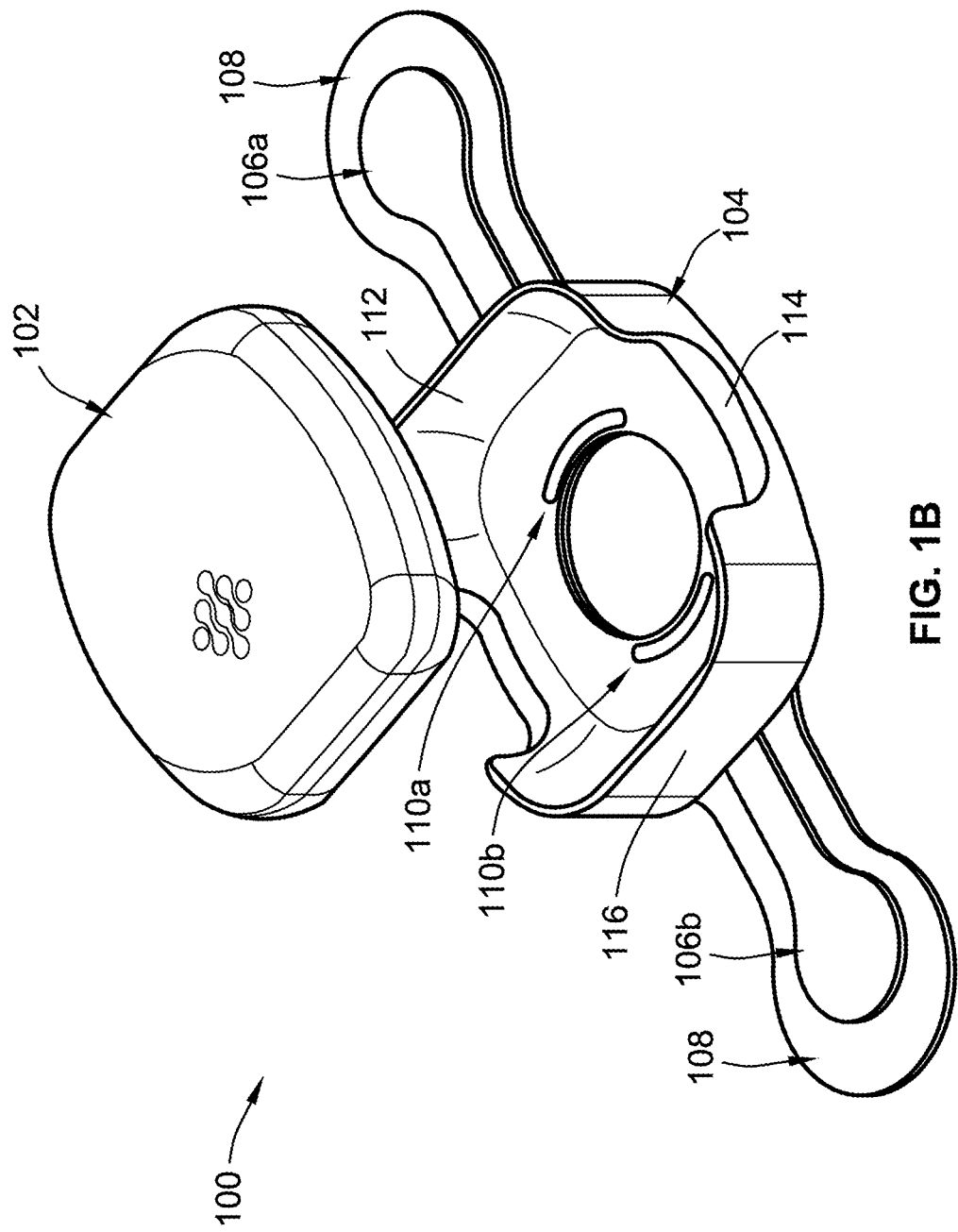
FIG. 1B illustrates a body of the electronic device of FIG. 1A separated from a base of the electronic device, according to some implementations of the present disclosure.

FIG. 1B illustrates the body 102 of the electronic device 100 separated from the base 104 of the electronic device 100. The base 104 is shown to have an inner surface 112 with a concave-in contour for receiving the body 102. The base 104 can include one or more cutouts or receded sidewalls 114 to facilitate removing or decoupling the body 102 from the base 104. The base 104 is configured to hold the body 102 in place when the body 102 is coupled to the base 104. The base 104 can hold the body 102 in place via a friction force created between the inner surface 112 and the housing of the body 102 when the body 102 is coupled to the base 104 as depicted in FIG. 1A. The housing of the body 102 can have a pressure fit with the base 104, holding the body 102 in place. With minimal modification, the body 102 can be secured to the base 104 using other methods.

In some implementations, the body 102 and the base 104 can include a latch for securing the body 102 to the base 104. For example, an outer surface 116 of the base 104 can include a recess (or catch) for receiving a lever or an arm attached to the body 102. In another example, the body 102 can include one or more protruding portions, and the inner surface 112 can include one or more recesses for catching the protruding portions of the body 102. These methods of securing the body 102 to the base 104 are non-limiting and are merely provided as examples.

The base 104 is further configured to provide an opening such that an electrode end 110a of the electrode 106a and an electrode end 110b of electrode 106b is accessible via the inner surface 112 of the base 104. Two electrodes 106a and 106b are shown as examples in FIGS. 1A-1B, but more than two electrodes can be coupled to the base 104. The electrodes 106 can be positioned on the adhesive 108. The adhesive 108 can secure the electrodes 106 in place on a skin of the user. In some implementations, the adhesive 108 can also secure the base 104 to the electrodes 106.

In some implementations, the electrodes 106 provided in the adhesive 108 have a male or female gender to them. Such that, complementary gendered electrodes are provided on a bottom of the base 104. That way, the adhesive 108 holds the male and/or female gendered electrodes to the skin of the user, and when the base 104 is coupled to the electrodes, the complementary gendered electrodes interface with the male and/or female gendered electrodes. The complementary gendered electrodes can snap onto the male and/or female gendered electrodes, securing the base 104 to the adhesive 108. Examples of gendered electrodes include adhesive button electrodes, electrocardiogram (ECG) electrodes, or any other adhesive electrode with a snap fastener.

Although one adhesive layer (the adhesive 108) is described, in some implementations, more than one adhesive layer can be used. For example, one adhesive layer can include one electrode, such that a number of adhesive layers correspond to a number of electrodes. In some implementations, more than one electrode can share an adhesive layer but not all electrodes share a same adhesive layer.

Although adhesives are described to keep the electrodes 106 on the skin of the user, other methods of keeping the electrodes 106 and the electronic device 100 on the user are envisioned. For example, depending on where the user wears the electronic device 100, a band can be provided such that the electronic device 100 is held in place by the band. The band can be a chest band.

Although the base 104 is included in the electronic device 100 as depicted in FIGS. 1A and 1B, in some implementations, the base 104 is not included. For example, the adhesive 108 with the electrodes 106 can be configured to mechanically hold the body 102 in place on the skin of the user while also electrically connecting the electrodes 106 to electronic components in the body 102. Methods of holding the body 102 in place can include using complementary electrodes as previously discussed in connection to securing the base 104 to the adhesive 108 and the electrodes 106. Gendered electrodes can be provided as the electrodes 106 and complementary gendered electrodes can be provided on the body 102. Such that, the complementary gendered electrodes on the body 102 snap onto the gendered electrodes provided on the adhesive layer.

Figure 2A:
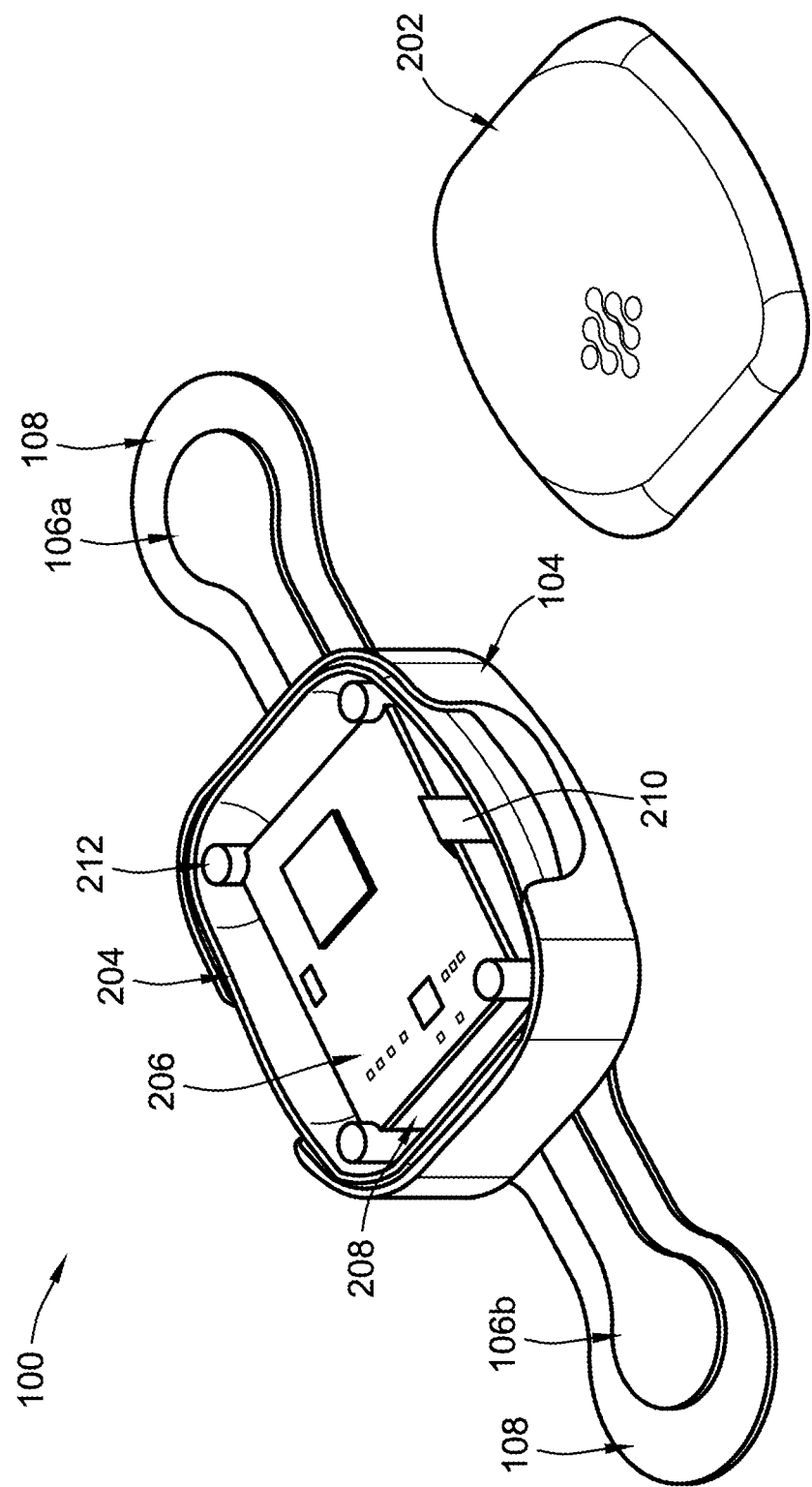
FIG. 2A illustrates an interior of the body of the electronic device of FIG. 1A, according to some implementations of the present disclosure.

Referring to FIG. 2A, an interior of the body 102 of the electronic device 100 of FIG. 1A is illustrated according to some implementations of the present disclosure. The housing of the body 102 is shown to include two portions, a top housing portion 202 and a bottom housing portion 204. The top housing portion 202 is configured to serve as a covering while the bottom housing portion 204 is configured to hold electronic components of the body 102. The bottom housing portion 204 can include a main printed circuit board (PCB) 206 and a mechanical holder 208 for preventing the main PCB 206 from moving. The bottom housing portion 204 can also include a flexible PCB connector 210 for connecting the main PCB 206 to other electronic components within the body 102. The bottom housing portion 204 can further include one or more bottom guides 212 for keeping the electronic components in the body 102 from moving laterally within the body 102. The one or more bottom guides 212 can match one or more top guides (not shown) for aligning the top housing portion 202 with the bottom housing portion 204.

Figure 2B:
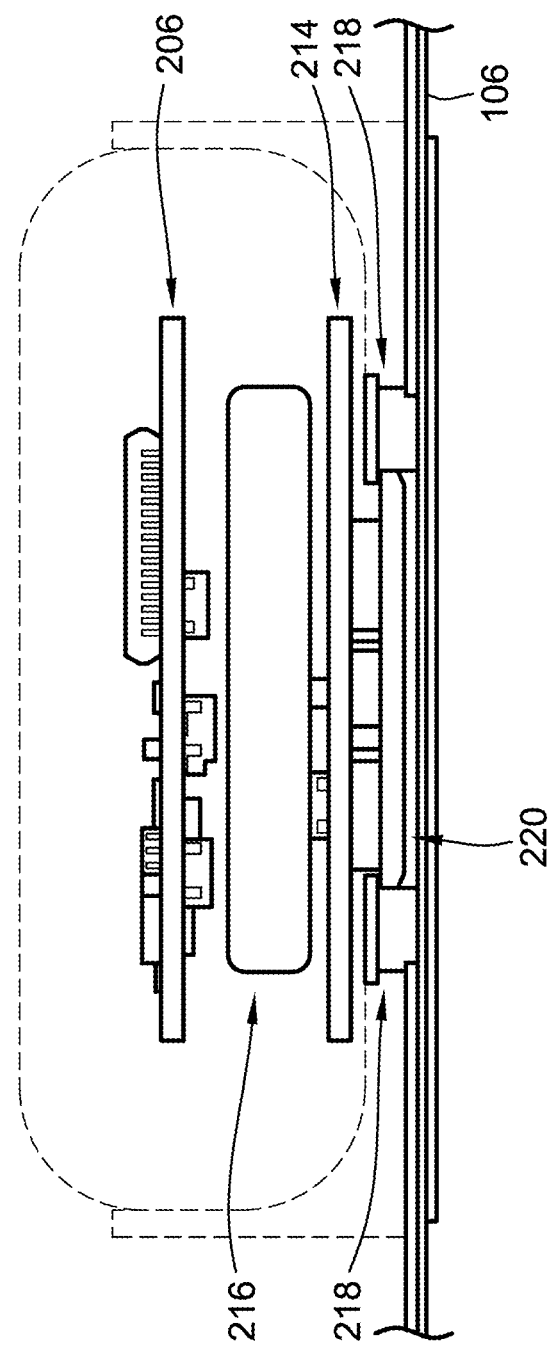
FIG. 2B illustrates an arrangement of the interior of FIG. 2A, according to some implementations of the present disclosure.

FIG. 2B illustrates an arrangement of the interior of FIG. 2A when the body 102 is coupled to the base 104, according to some implementations of the present disclosure. In some implementations, multiple printed circuit boards (PCBs) can be provided in the body 102 according to a form factor of the body 102. The multiple PCBs allow for vertically stacking the PCBs to conserve space and reduce wiring costs when compared to using one PCB. The main PCB 206 can include one or more processors, memory, filters, etc. The one or more processors can include multicore processors, graphics processing units (GPUs), artificial intelligence (AI) accelerator chips, neural processors, etc. A sensor PCB 214 can be provided that includes sensors, analog to digital converters, digital to analog converters, memory, etc. A battery 216 can be provided to power the multiple PCBs.

At the bottom of the body 102, a housing window material 220 can be provided to protect the body 102 from outside contaminants as well as provide a clear path for optical sensors, imaging sensors, thermal imaging sensors, laser sensors or other sensors performing non-contact measurements on the skin of the user. The imaging sensors can provide an image of the skin of the user, and the thermal imaging sensors can provide a thermal image of the skin of the user. Metal connectors 218 are provided to facilitate connection of the electrodes 106 to the sensor PCB 214.

Figure 3:
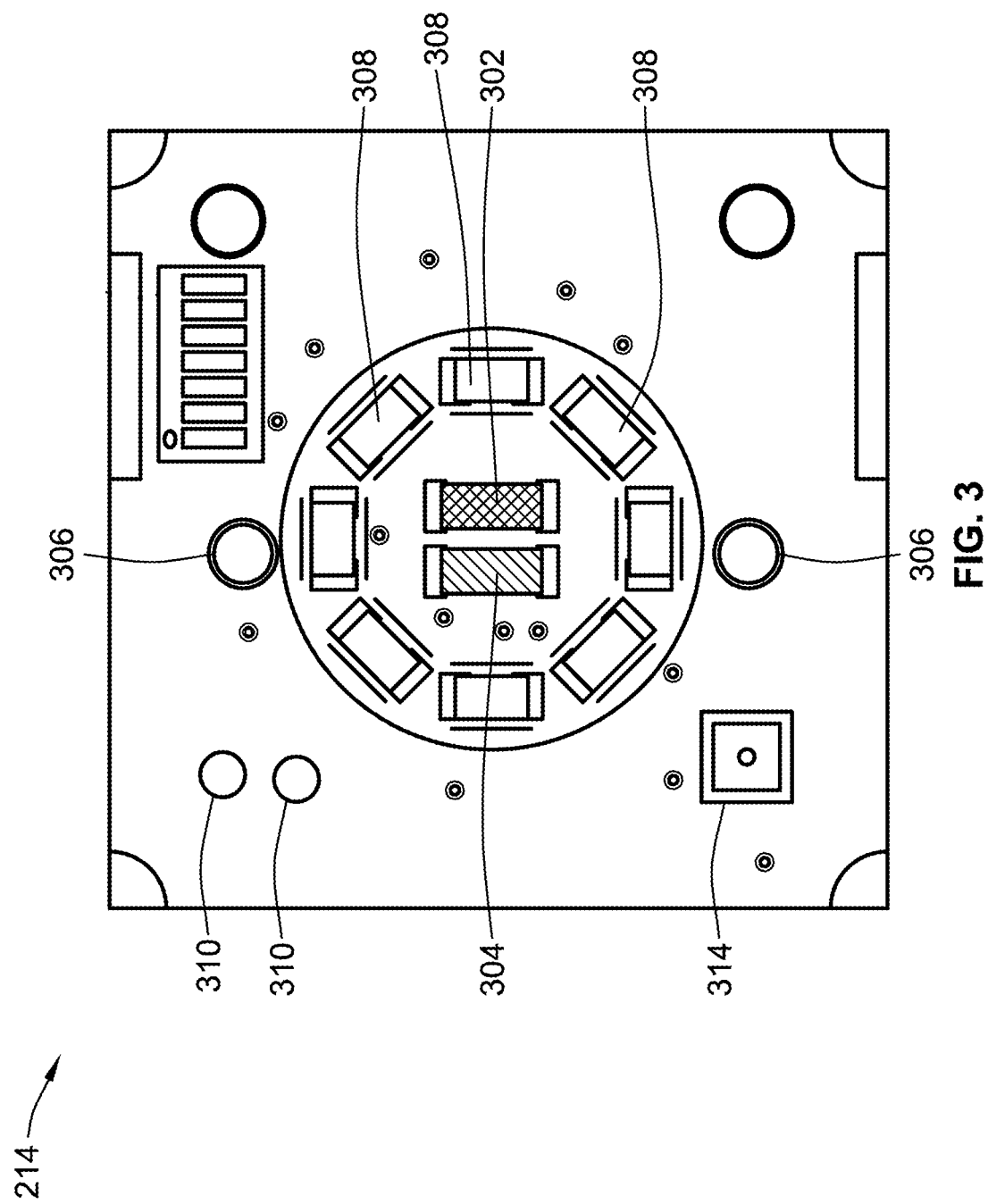
FIG. 3 illustrates a sensor board for the electronic device of FIG. 1A, according to some implementations of the present disclosure.

FIG. 3 illustrates a bottom side of the sensor board 214 of the electronic device 100 depicted in FIG. 1A, according to some implementations of the present disclosure. The sensor board 214 can include one or more emitters, for example, one or more light emitting diodes (LEDs). The one or more LEDs can be different LEDs, for example, the sensor board 214 provides a red LED 304 and an infrared LED 302. The red LED 304 can emit light in a wavelength range between 600 nm and 750 nm, for example, at about 650 nm wavelength. The infrared LED 302 can emit light in a wavelength range between 850 nm and 1000 nm, for example, at about 940 nm wavelength. The sensor board 214 can include one or more photodetectors, for example, photodiodes 308. The photodiodes 308 can measure both red and infrared light. The photodiodes 308 can be arranged around a center as shown in FIG. 3. The photodiodes 308 can be arranged around the red LED 304 and the infrared LED 302. The combination of the one or more emitters and the one or more photodetectors can be used as an optical array measurement system. Arranging the photodiodes 308 around the center can introduce redundancy that minimizes effects of noise attributed to the skin of the user moving, a heart of the user moving, and so on. In an example, arranging optical sensor arrays around a center can improve robustness of oxygen level sensor values obtained via the photodetectors and the emitters. Although the photodiodes 308 are arranged around the center, other photodiode arrangements are within the scope of the present disclosure.

The sensor board 214 can include one or more charging pads 310. The one or more charging pads 310 are configured to conduct charge for charging a battery connected to the sensor board 214, for example, the battery 216 of FIG. 2B. The charging pads 310 can be made of copper.

The sensor board 214 can include one or more electrode pads 306 for facilitating sending and receiving signals from electrodes, for example, the electrodes 106 of FIG. 1A. Although two electrode pads 306 are depicted in FIG. 3, the number of electrode pads 306 can vary based on a number of the electrodes 106.

The sensor board 214 can include a temperature sensor 314. The temperature sensor 314 can be a contactless temperature sensor configured to obtain temperature of the user without contacting a body part of the user. The sensor board 214 can include one or more connecting pads for connecting the sensor board 214 to other PCBs in the electronic device 100.

Figure 4A:
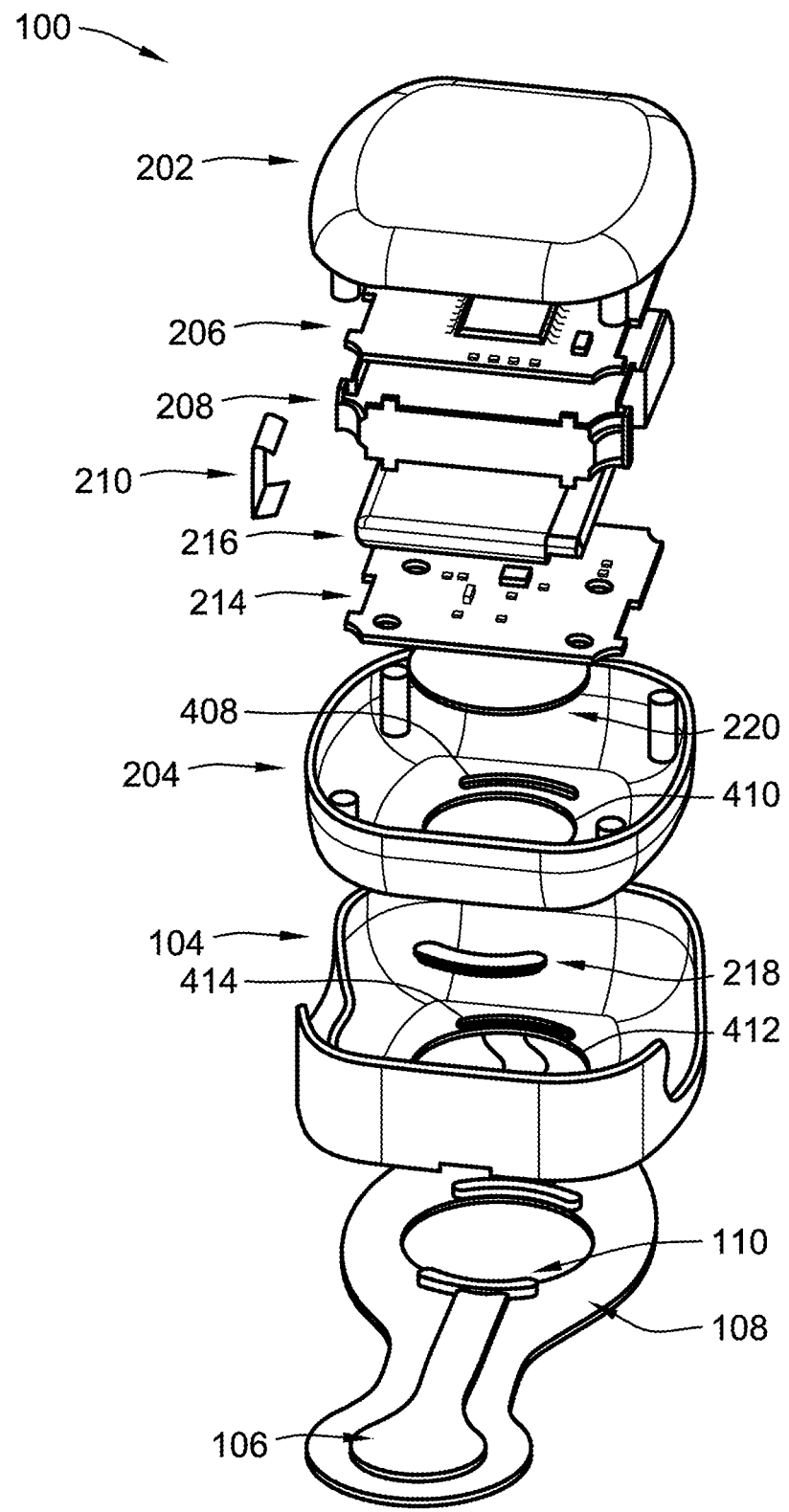
FIG. 4A illustrates components in the electronic device of FIG. 1A, according to some implementations of the present disclosure.

FIG. 4A illustrates components in the electronic device 100 of FIG. 1A, according to some implementations of the present disclosure. The electronic device 100 includes the top housing portion 202 and the bottom housing portion 204. Enclosed within the top housing portion 202 and the bottom housing portion 204 are the main PCB 206, the holder 208, the flexible PCB connector 210, the battery 216, and the sensor board 214. The bottom housing portion 204 can include one or more housing openings, for example, the housing openings 408, and/or one or more housing windows, for example, the housing window 410.

The housing window material 220 is engineered to cover the housing window 410. The housing window material 220 protects the electronic components of the body 102 from outside elements, for example, liquid, dust, and/or other particles. The housing window material 220 prevents these outside elements from entering the body 102 via the housing window 410. The housing window material 220 can be a translucent material including plastic, sapphire crystals, mineral crystals, plexiglass, hesalite crystals, glass, etc. Although the housing window material 220 and the housing window 410 are shown to have a circular shape, other shapes can be used. For example, the housing window material 220 and the housing window 410 can be shaped as a square, a rectangular, a polygon, etc.

The housing window 410 is provided as an example, but more than one housing window can be provided. For example, the electronic device 100 can have as many housing windows as a total number of photodetectors and light emitters. In another example, the electronic device 100 can have as many housing windows as a total number of line of sight sensors, for example optical sensors, imaging sensors, thermal imaging sensors, laser sensors, etc. Each respective photodetector and/or light emitters can have a dedicated housing window or can share a housing window with another photodetector and/or light emitter. For example, two light emitters can share a housing window, two photodetectors share another housing window, three photodetectors share yet another housing window, and one photodetector has its dedicated housing window. A housing window material can be provided for all housing windows of the bottom housing portion 204.

The housing openings 408, different from the housing window 410, are configured to allow electrical connections to the sensor board 214 from components outside the body 102. The housing openings 408 can take the shape of one or more metal connectors 218 that interface with the housing opening 408. The one or more metal connectors 218 are designed to plug the housing openings 408 such that the housing openings 408 are sealed when the body 102 is coupled to the base 104 as depicted in FIG. 1A. In some implementations, when in the configuration as depicted in FIG. 1A, the electronic device 100 is waterproof.

In some implementations, the base 104 includes a base window 412. The base window 412 is shown as substantially circular, but other shapes can be envisioned. Unlike the housing window 410, the base window 412 is not filled with any material and is just an opening that substantially matches the housing window 410 on the body 102. When the body 102 is coupled to the base 104, the housing window 410 and the base window 412 are aligned such that sensors on the sensor board 214 can send light from the sensor board 214 to the base window 412 via the housing window 410, and the sensors on the sensor board 214 can receive light from the base window 412 via the housing window 410.

In some implementations, the base 104 includes one or more electrode openings 414 for receiving the electrodes 106. The electrode openings 414 can have a shape that substantially matches the one or more metal connectors 218. The electrode openings 414 can also have a shape that substantially matches the electrode ends 110 of the electrodes 106.

In some implementations, one or more metal connectors 218 are configured to receive the electrode ends 110. The electrode ends 110 protrude from the one or more electrode openings 414, and the one or more metal connectors 218 snap onto the electrode ends 110. When snapped onto the electrode ends 110, the one or more metal connectors 218 have an electrical connection to the electrodes 106. When snapped onto the electrode ends 110, the one or more metal connectors 218 hold the base 104 in place between the electrodes 106 and the one or more metal connectors 218.

In some implementations, the one or more metal connectors 218 are configured to be inserted in the one or more electrode openings 414 in the base 104 (from the inner surface of the base 104). When inserted, the one or more metal connectors 218 make contact with the electrode ends 110 inserted from the outer surface of the base 104. The one or more metal connectors 218 and the electrode ends 110 are designed to fit snugly into the one or more electrode openings 414.

In some implementations, the adhesive 108 not only supports and secures the electrodes 106 on the user's skin, but a top layer of the adhesive 108 contacting the base 104 can removably attach to the outer surface of the base 104. The base 104 can be designed to plug in and out the body 102 and send ECG electrical signals to the sensor board 214 of the body 102. The base 104 can be designed to replace the adhesive electrodes 106 easily if the adhesive electrode 106 is broken or old.

Figure 4B:
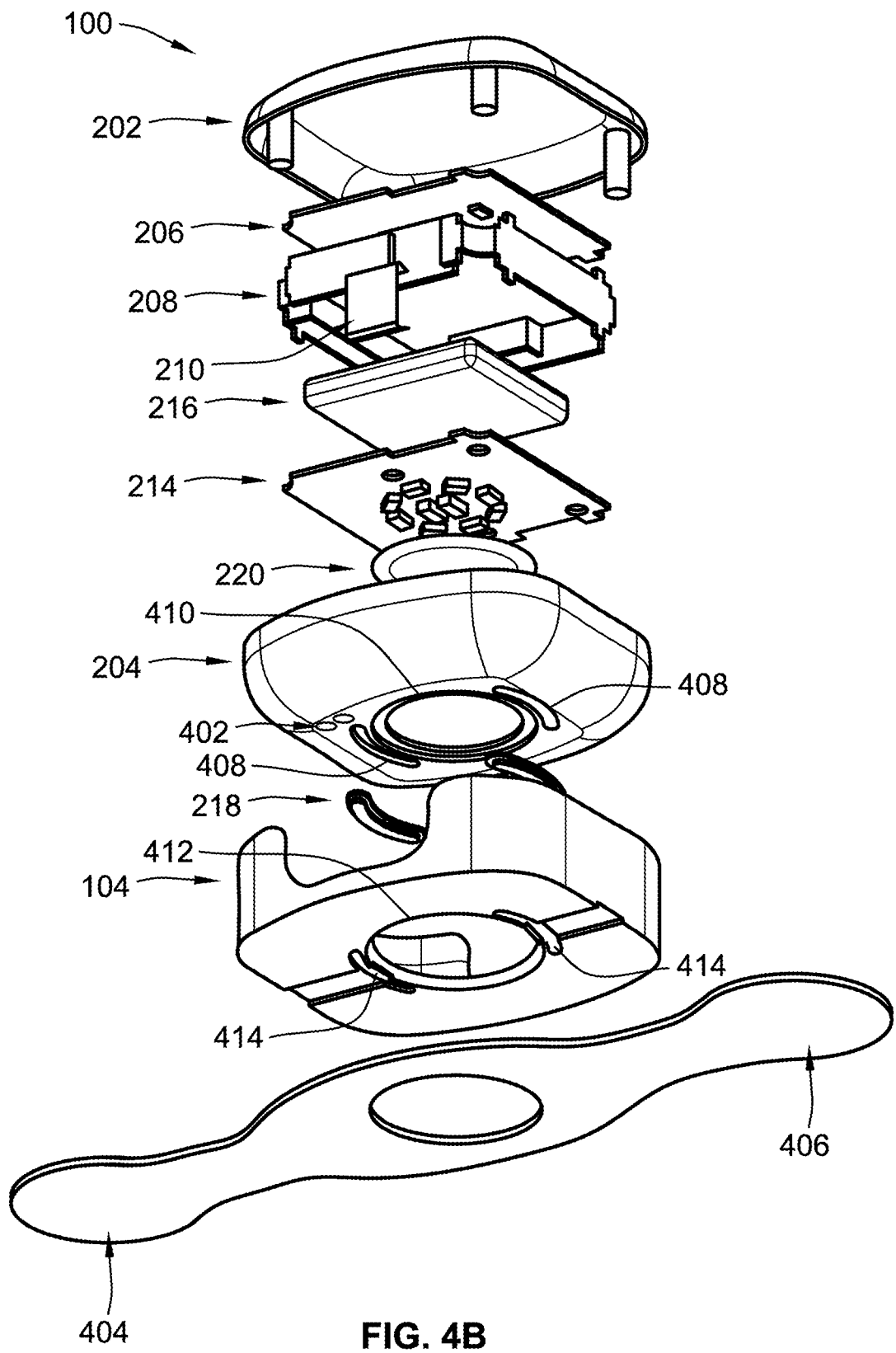
FIG. 4B illustrates the components in FIG. 4A from another perspective.
Figure 5A:
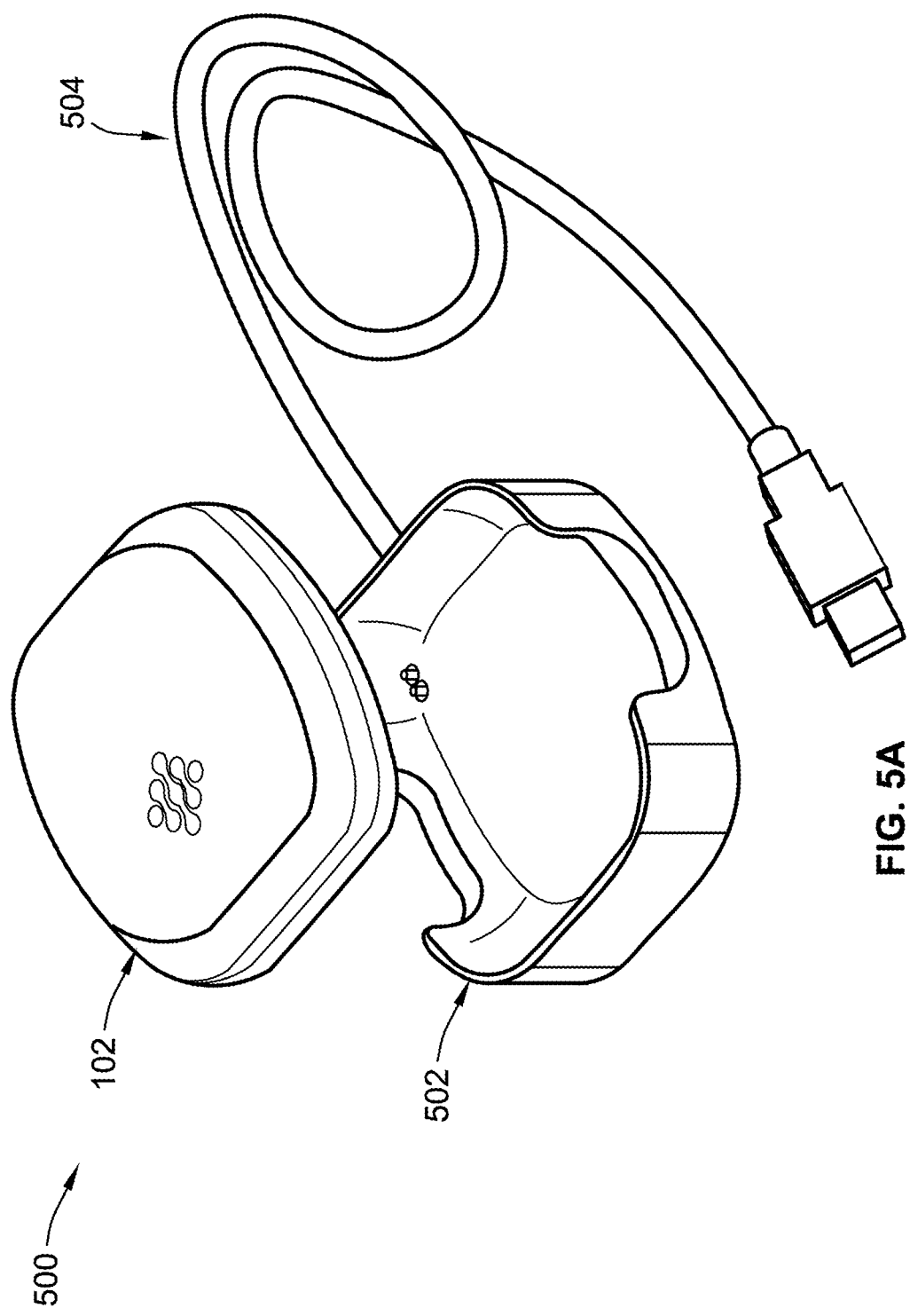
FIG. 5A illustrates the body of the electronic device of FIG. 1A separated from a charging station, according to some implementations of the present disclosure.

FIG. 4B illustrates the components in FIG. 4A from another perspective. In FIG. 4B, a two electrode configuration can be used for ECG measurements. For example, electrode sitting at position 404 above the adhesive 108 can represent an LA terminal for ECG measurements, and electrode sitting at position 406 above the adhesive 108 can represent the RA terminal. Also in FIG. 4B, one or more charging ports 402 are provided for interfacing the body 102 to a charging station. FIG. 5A illustrates a system 500 including the body 102 of the electronic device 100 of FIG. 1A separated from a charging station 502, according to some implementations of the present disclosure. The charging station 502 is configured to receive the body 102 similar to the base 104 in FIGS. 1A and 1B. The charging station 502 can have a charging cable 504 such that when the body 102 is cradled in the charging station 502, the charging cable 504 connects the body 102 to a power supply (not shown). In some implementations, the charging cable 504 connects the body 102 directly to a computer or other electronic device to also enable data transfer from the body 102 to the computer. In some implementations, the charging cable 504 is a Universal Serial Bus (USB) cable or a USB-C cable. The charging cable 504 can connect the body 102 to a computer's USB port to enable charging.

FIG. 5B illustrates an interior of the charging station 502 when coupled to the body 102 of the electronic device 100 of FIG. 1A, according to some implementations of the present disclosure. The charging station 502 is shown to include a charging PCB 506 with one or more terminals 508 that interface with the one or more charging ports 402 on the body 102. FIG. 5B illustrates an example of wired charging, but in some implementations, the charging station 502 can wirelessly charge the battery 216 included in the body 102. That is, instead of having the one or more terminals 508, the charging PCB 506 can include one or more coils for creating a changing magnetic field for charging the battery 216. The body 102 can include on any of the main PCB 206, the sensor board 214, or any other PCB, a coil for sensing the changing magnetic field to induce a current for charging the battery 216. Near field communication (NFC), inductive charging, or other wireless charging methods can be integrated with the charging station 502 and the electronic device 100.

Figure 6:
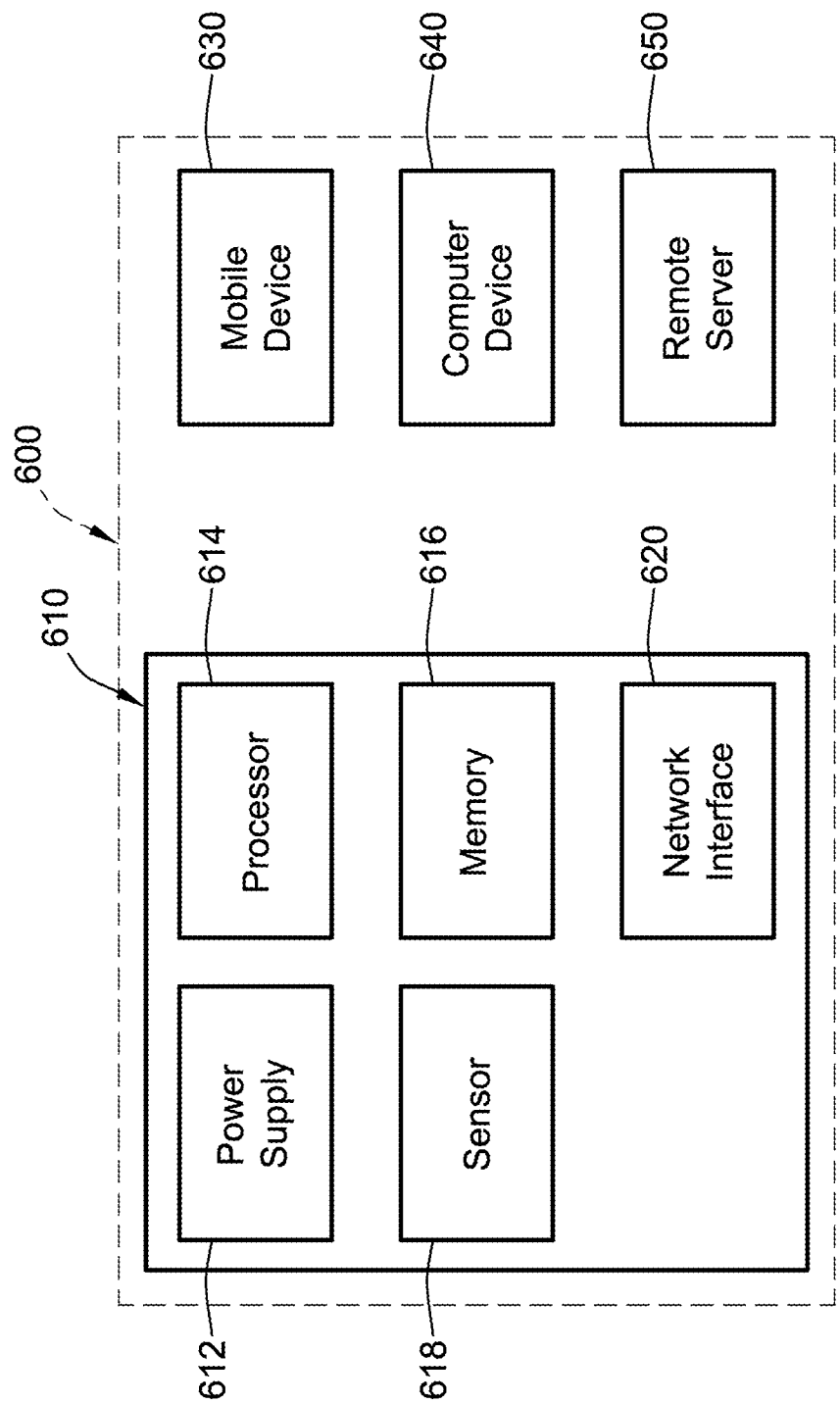
FIG. 6 is a block diagram of a system for monitoring health metrics of the user, according to some implementations of the present disclosure.

FIG. 6 is a block diagram of a system 600 for monitoring health metrics of a user, according to some implementations of the present disclosure. The system 600 includes an electronic device 610, a mobile device 630, a computer device 640, and/or a remote server 650. The electronic device 610 is similar to or the same as the electronic device 100 discussed in connection to some implementations of the present disclosure. The electronic device 610 can interface with the mobile device 630 and/or the computer device 640. The mobile device 640 and/or the computer device 640 can interface with the remote server 650. To simplify discussion, the singular form will be used for all components identified in FIG. 6 when appropriate, but the use of the singular does not limit the discussion to only one of each such component.

The electronic device 610 can include a power supply 612. The power supply 612 includes a battery (e.g., the battery 216) and circuitry that interfaces the battery with the other components of the electronic device 610. An example of the battery is a 3.7V, 500 mAh lithium polymer (LiPo) battery.

The electronic device 610 can include a sensor 618. As indicated above with respect to components in FIG. 6, the sensor 618 can be one or more sensors. The sensor 618 can include a temperature sensor, a pulse oximeter, an accelerometer, a gyroscope, a magnetometer, a radar sensor, an impedance e spectroscopy unit, optical array sensors, a photoplethysmogram (PPG) sensor, an ECG sensor, a microphone array, a camera, a thermal imaging camera, one or more lasers, ultrasonic vibration sensors, or any combination thereof. The sensor 618 can include an inertial measurement unit (IMU) which includes the accelerometer, the gyroscope, and the magnetometer. The IMU can generate data for indoor navigation, step counting, walking speed, running speed, sleep monitoring, and motion of the user. The sensor 618 can generate physiological data including a glucose level of the user, a blood pressure of the user, a blood oxygen saturation (SpO2) of the user, a heart rate of the user, an ECG waveform of the user, a level of skin moisture of the user, a humidity level, a temperature of the user, an activity level of the user, a body position of the user, a body orientation of the user, or any combination thereof.

In some implementations, visual indicators can be used for signaling. For example, visual indicators can signal that the electronic device 100 is capturing data, battery level of the battery 216 is low, that there is an issue to troubleshoot, etc. For example, the logo 103 can light up in green color during data capture. The logo 103 can turn red if the battery is low or if there if some issue to troubleshoot. Although color is used as an example, the logo 103 can incorporate sequence of flashes and brightness to distinguish between the different signaling.

In some implementations, the sensor 618 senses ECG via electrodes (e.g., the electrodes 106 of FIG. 1A). The electrodes are stuck to the skin of the user with adhesive. In an embodiment, ECG uses three electrodes (left arm LA, right arm RA, and right leg RL), but the electronic device 610 can use two electrodes where RA uses one of the electrodes 106 and LA uses the other of the electrodes 106. The sensor 618 can sense PPG using light emitters (e.g., the red LED 304 and the infrared LED 302 of FIG. 3) and photodetectors (e.g., the photodiodes 308 of FIG. 3). The sensor 618 can sense temperature and humidity using a dedicated chip (e.g., the temperature sensor 314 of FIG. 3).

In some implementations of the present disclosure, the electronic device 610 can generate data pertaining to one or more skin parameters including skin moisture, skin oiliness, skin firmness, or a combination thereof. Skin moisture can be determined in multiple ways, for example, by using humidity sensors included in the sensor 618 to measure humidity around the skin, using capacitive sensors included in the sensor 618 to determine skin capacitance, or a combination thereof. A higher capacitance indicates a higher hydration level of the skin. An optical array sensor included in the sensor 618 can use light reflections to determine skin oiliness where an oilier skin reflects more light than a less oily skin. A mechanically oscillating sensor tip included in the sensor 618 or a body of the electronic device 610 can be used to measure skin elasticity where a change in frequency of oscillation between free-space oscillation and oscillation when applied to the skin. The higher the change in frequency of oscillation, the greater the skin elasticity.

The electronic device 610 can include a processor 614. The processor 614 can be one or more microprocessors, one or more microcontroller units, one or more multicore processors, one or more GPUs, one or more AI accelerator chips, one or more neural processors, or any combination thereof. The processor 614 is configured to execute instructions stored on the memory 616. The memory 616 acts as a non-transitory computer readable medium which stored instructions can be executed by the processor 614. The memory 616 can reside on one or more PCBs of the electronic device 610. In some implementations, the memory 616 can store (temporarily and/or permanently) data generated by the sensor 618 of the system 600. In some implementations, the memory 616 includes non-volatile memory, static random access memory (RAM), volatile RAM, electrically erasable programmable read only memory (EEPROM) memory, flash memory, or any combination thereof. In some implementations, the memory 616 is a removable form of memory (e.g., a memory card).

In some implementations, the memory 616 can store about 1-week data when having the electronic device 610 sense or generate data from the sensor 618 every 15 minutes. The memory capacity can be as low as 1344 kbyte for storing week-long data under these parameters. In some implementations, the memory 616 has a 2 Mbyte capacity. The preceding hardware configuration is provided as an example, but other hardware configurations can be used to allow for longer duration storage at more frequent sampling intervals.

The processor 614 in cooperation with the memory 616 can process data generated by the sensor 618 to obtain ECG waveforms, glucose levels, blood pressure, heart rate, blood oxygen level, temperature, humidity, or a combination thereof. Blood pressure can be determined from ECG and/or PPG. Heart rate can be determined from the ECG waveform and/or from a PPG waveform. Heart rate can also be determined from the microphone array listening to the user's heartbeat. Glucose level can be determined from the ECG waveform using heart rate data. Glucose level can also be determined via a radar sensor that emits high-frequency radio waves to measure electrical variations in blood properties which can be analyzed to estimate glucose levels. SpO2 can be determined from infrared and red PPG waveforms, temperature, and humidity. Alternative methods for determining glucose, blood pressure, and heart rate exist and those listed above are merely examples. Table I provides an example of sensor values and information that can be gleaned from the sensor values according to some implementations of the present disclosure.

The electronic device 610 can include a network interface 620 for communicating with the mobile device 630 and/or the computer device 640. The network interface 620 can be a wired interface or a wireless interface. For example, the network interface 620 can support Wi-Fi, Bluetooth, Bluetooth Low Energy (BLE), cellular networks like 3G, 4G, 5G, etc. The electronic device 610 can support subscriber identity module (SIM) and/or embedded SIM for use with any of the wired and/or wireless interfaces. The network interface 620 can also include global positioning system (GPS) receiver for generating location data of the electronic device 610. In some implementations, the network interface 620 can use wireless technologies supported to allow the processor 614 to run an indoor positioning system. For example, the network interface 620 with Wi-Fi support can be used for Wi-Fi based positioning systems. In some implementations, the network interface 620 can include an ultra-wide band (UWB) chip for precise indoor location positioning for monitoring movement in hospitals, nursing homes, patient homes, offices, etc. In some implementations, the network interface 620 can receive a semantic location of the electronic device 610 based on the generated location data. For example, based on GPS receiver location data, the electronic device 610 can be determined to be at the Golden State Bridge (semantic location).

In some implementations, the network interface 620 includes NFC or other wireless technologies for automatic setup and wireless pairing of the electronic device 610 with the computer device 640 and/or the mobile device 630 (e.g., a smartphone/other device that exchanges settings via NFC). The network interface 620 with NFC can then be used to automatically transmit health metrics from the electronic device 610 to the mobile device 630.

The processor 614 can perform low-level functions of acquiring data generated by the sensor 618, uploading the data generated to the remote server 650, and locally managing battery power consumption by performing power management on the electronic device 610 using, for example, wake and sleep cycles. For example, to extend battery life, the processor 614 can use BLE for reducing power consumption during wireless communication, can advertise to other devices a wireless identification of the electronic device 610 for only a short period of time (e.g., 0.5 seconds) before going into low power mode. The processor 614 can turn off all peripherals and the sensor 618 after measuring physiological data. The processor 614 can have more than one power mode, for example, the processor 614 can have a standard power mode, a low power sleep mode, a stop mode, a standby mode, or any combination thereof. The standby mode can exhibit the lowest power consumption.

The processor 614 can employ data compression to reduce memory usage of the data generated by the sensor 614. For example, ECG data can contain many data points requiring a large memory space. The processor 614 can employ discrete wavelet transform (DWT) to filter high frequency values so that size of the ECG data can be reduced.

The electronic device 610 can monitor and gather physiological data indicative of health metrics of the user. The electronic device 610 can send the physiological data to the mobile device 630 and/or the computer device 640. Examples of the mobile device 630 include a smartwatch, a tablet, a smartphone, a fitness tracker, a laptop computer, etc. Examples of the computer device 640 include a desktop computer, a smart television, a desktop or laptop of a caregiver separate from the user, etc. The mobile device 630 can relay the physiological data to the remote server 650 for analysis or can analyze some of the physiological data. The mobile device 630 can combine the physiological data with other context data or other sensor data on the mobile device 630 before analyzing or sending to the remote server 650. The remote server 650 can be a cloud server running one or more applications for supporting functionality attributed to the electronic device 610. The mobile device 630 can display analysis results for the user.

In some implementations, the remote server 650 is a cloud server that stores the physiological data in a database (e.g., dynamodb). The network interface 620 can send the physiological data to the remote server 650 in a JavaScript Object Notation (JSON) data format. The remote server 650 can receive the physiological data (e.g., glucose level, blood pressure, heart rate, oxygen level, temperature, humidity, activity level, etc.) and estimate the health of the user. The physiological data can be date or time stamped and can also include one or more locations where the physiological data was gathered. The remote server 650 can receive raw data from the sensor 614 and estimate the health of the user. The remote server 650 can combine the raw data from the sensor 614 and/or the physiological data from the electronic device 610 or the mobile device 630 with patient data in an electronic health record (EHR) of the user to estimate the health of the user.

For example, glucose level history can indicate change of the glucose level in the user's blood and enable estimating whether the user is at risk for diabetes. In some implementations, a diabetes type (e.g., type 1 diabetes or type 2 diabetes) or normal state can be indicated by the glucose level. The remote server 650 can use artificial intelligence to predict how much the user's glucose level will change in different time periods, for example, how much the user's glucose level will change within several hours, within a next day, within several days, etc.

In some embodiments, the artificial intelligence algorithms can run on the electronic device 610. On-device machine learning models can be used in combination with the sensor 618 to infer the condition or health state of the user of the electronic device 610.

In an embodiment, the artificial intelligence used can include a probabilistic neural network (PNN). The PNN can be trained using, for example, three days' worth of data generated by the sensor 618 such that the electronic device 610 learns a specific pattern of the user.

The remote server 650 can use blood pressure and heart rate history to estimate heart status of the user. The oxygen level can be used to estimate behavior of the user's lungs, blood flow, and hemoglobin count in the blood. Temperature and humidity measurements can be used to estimate the user's health and also for calibrating the sensor 618.

The remote server 650 can provide feedback based on calculations made from the physiological data. For example, if the calculations indicate that the user's health is in an abnormal state, the remote server 650 can send a notification alert to the mobile device 630. The notification alert can be an alert that pops up on a mobile app running on the mobile device 630, an SMS or a push notification to the phone number of the mobile device 630, an email opened on the mobile device 630, or any combination thereof.

In some implementations, the notification alert is sent by the remote server 650 to both the user and a caregiver of the user (e.g., a doctor, nurse, physical therapist, trainer, etc.). The user and the caregiver can be provided access to download a report of the user's health data.

TABLE 1

Example sensors with captured data and use of the captured data

| No | Sensors | Captured Data | Data Format | Example use of data |
|---|---|---|---|---|
| 1 | Temperature/ Humidity | Temperature and humidity values | [Temp1, Hum1], [Temp2, Hum2], [Temp3, Hum3], . . . | Temperature and humidity of body(chest), used for: (1) body temperature values, (2) calibrating other measurements such as blood pressure, glucose, etc. (3) skin humidity/moisture |
| 2 | Accelerometer | 3 axis accelerometer values | [accel1, accel2 . . . ] | Acceleration values used for measuring movement of human body and pose angle in order to compensate the signal change based on change of body pose (lying, stand . . . ) |
| 3 | Optical Sensor values | IR (940 nm) and Red (650 nm) LED sensor values (ADC) | [IR1, RED1], [IR2, RED2], [IR3, RED3], . . . | Determining blood oxygen level (SPO2), blood pressure, calibration for glucose level |
| 4 | ECG Sensor | ADC values from ECG electrodes | [ADC1, ADC2, . . . ] | This ADC value is used for measuring medical grade |

TABLE 1-continued

Example sensors with captured data and use of the captured data

| No | Sensors | Captured Data | Data Format | Example use of data |
|---|---|---|---|---|
| 5 | Impedance Sensor | Complex Impedance sensor values (VCO) | [Vph1, Vmag1], [Vph2, Vmag2], [Vph3, Vmag3], ... | electrocardiogram signals Used for measuring impedance change in high frequency electromagnetic field. Purpose is to measure glucose level directly driven by impedance change of chest skin |

In some embodiments, additional functionality and firmware updates can be made to the electronic device 610 via the network interface 620. When the electronic device 610 is directly connected to a network (e.g., a WiFi network, a cellular network, etc.) or connected to another device (e.g., the mobile device 630, the computer device 640, etc.), the electronic device 610 can ping a server (e.g., the remote server 650) to check for firmware updates. If a firmware update is available on the remote server 650, then the electronic device 610 can download the firmware update from the remote server 650 (if directly connected to the remote server 650) or can receive the firmware update from the mobile device 630 or the computer device 640 (if indirectly connected to the remote server 650). The firmware update can be installed and executed on the electronic device 610 after an automated reboot of the electronic device 610. Firmware updates can be used to enable new functionality, health metrics monitoring, machine learning models, algorithms, security patches, or any combination thereof. Although described in the context of receiving firmware updates, the electronic device 610 can receive device settings and configurations in a similar fashion via a server (e.g., the remote server 650).

Embodiments of the disclosure provide a reusable design of the electronic device where sensors can be swapped in and out using different PCBs. The industrial design of the electronic device facilitates measuring ECG values, impedance values, optical sensor values, etc., simultaneously. More sensors are packed into the small form factor such that its size is comparable to other wearable medical products with only one sensor.

While the present disclosure has been described with reference to one or more particular implementations, those skilled in the art will recognize that many changes may be made thereto without departing from the spirit and scope of the present disclosure. Each of these embodiments and implementations and obvious variations thereof is contemplated as falling within the spirit and scope of the present disclosure, which is set forth in the claims that follow.

What is claimed is:

1. A smart patch to monitor health metrics of a user, comprising:
   an adhesive for attaching the smart patch to a skin of the user;
   at least two electrodes attached to the adhesive and capable of electrically coupling to the user;
   a cradle removably coupled to the adhesive, the cradle having a cradle opening for access to the skin of the user and at least two electrode openings, wherein when the cradle is coupled to the adhesive, the at least two electrodes protrude from a top surface of the cradle through the at least two electrode openings; and
   a computing device that is selectively removable from the cradle and including:
      a housing having a top housing portion and a bottom housing portion;
      a main printed circuit board (PCB);
      a sensor window in the bottom housing portion of the housing;
      a battery;
      circuitry coupled to the at least two electrodes to measure electrical activity from the skin of the user;
      one or more sensors configured to interface with the skin of the user, through the sensor window and the cradle opening, to generate physiological data associated with the health metrics of the user;
      a sensor PCB including PCB contacts and configured to electrically connect the PCB contacts to the one or more sensors;
      a flexible PCB connector configured to electrically connect the main PCB to the sensor PCB;
      at least two metal connecting pads, wherein when the computing device is coupled to the cradle, the at least two electrodes protruding from the surface of the cradle being electrically connected to the PCB contacts via the at least two metal connecting pads; and
      a mechanical holder configured to secure the battery such that the battery is sandwiched between the sensor PCB and the main PCB, the mechanical holder further securing the main PCB to the bottom housing portion.

2. The smart patch of claim 1, wherein the one or more sensors comprise a photoplethysmogram (PPG) sensor, and when the computing device is secured to the cradle, the PPG sensor interfaces with the user via the sensor window and the cradle opening by (i) emitting light that passes through the sensor window and the cradle opening, and (ii) receiving reflected light that passes through the sensor window and the cradle opening.

3. The smart patch of claim 1, wherein the sensor window of the housing is made from translucent materials including plastic, sapphire crystals, mineral crystals, plexiglass, hesalite crystals, or glass.

4. The smart patch of claim 1, wherein:
   the adhesive is configured to secure the at least two electrodes to the skin of the user, wherein the at least two electrodes are disposed in the adhesive such that a first end of each of the at least two electrodes contacts the skin of the user and a second end of each of the at least two electrodes interfaces with the computing device.

5. The smart patch of claim 1, wherein the computing device comprises at least one memory unit to store physiological data associated with the user, the physiological data being captured from the at least two electrodes and the one or more sensors.

6. The smart patch of claim 1, further comprising:
a network interface configured to:
communicate with one or more external devices, provide a physical location of the smart patch as location data, or both,
wherein the network interface supports cellular, Wi-Fi, Bluetooth, Bluetooth Low Energy, GPS, or any combination thereof.

7. The smart patch of claim 1, wherein the computing device is removably coupled to the cradle via a pressure fit between the computing device and the cradle, a latch between the computing device and the cradle, or a fastener between the computing device and the cradle.

8. The smart patch of claim 1, wherein the computing device is waterproof, the adhesive is waterproof, the at least two electrodes are waterproof, or any combination thereof.

9. The smart patch of claim 1, wherein the generated physiological data includes a glucose level of the user, a blood pressure of the user, a blood oxygen level of the user, a heart rate of the user, an electrocardiogram (ECG) waveform of the user, a level of skin moisture of the user, a temperature of the user, an activity level of the user, a body position of the user, an image of a skin of the user, a thermal image of the skin of the user, or any combination thereof.

10. The smart patch of claim 1, wherein the computing device is configured to removably couple to a charging station such that when the computing device is coupled to the charging station, the computing device is not coupled to the cradle.

11. The smart patch of claim 10, wherein the computing device further includes one or more charging ports configured to removably couple to the charging station, the one or more charging ports configured to facilitate charging of the battery by the charging station.

12. The smart patch of claim 10, wherein the battery is wirelessly charged by the charging station when the computing device is coupled to the charging station.

13. The smart patch of claim 1, wherein the one or more sensors include a temperature sensor, a pulse oximeter, optical array sensors, an impedance measurement unit, an impedance spectroscopy measurement unit, a radar sensor, inertial measurement unit (IMU), an accelerometer, a gyroscope, a magnetometer or a combination thereof.

14. The smart patch of claim 1, wherein the at least two electrodes include electrocardiogram (ECG) electrodes.

15. The smart patch of claim 1, wherein the computing device further comprises:
a near field communication (NFC) module configured to be communicatively coupled to a second NFC module of at least one electronic device; and
a wireless interface configured to communicate with the electronic device via an established wireless link.

16. The smart patch of claim 1, wherein the at least two metal connecting pads include snap fit connections with the at least two electrodes protruding through the at least two electrode openings of the cradle, the at least two metal connecting pads being configured to hold the cradle in place when coupled to the at least two electrodes.

* * * * *